(12) United States Patent
Hsieh

(10) Patent No.: US 11,759,330 B2
(45) Date of Patent: Sep. 19, 2023

(54) SUPPORTING MEMBER AND SUPPORTING MEMBER ASSEMBLY FOR IMPLANTATION INTO OR BETWEEN SUBJECTS BONES, AND TEMPLATE PLUG AND TAMPER CORRESPONDING TO THE SAME

(71) Applicant: NATIONAL TAIWAN UNIVERSITY HOSPITAL JINSHAN BRANCH, New Taipei (TW)

(72) Inventor: Jui-Yang Hsieh, New Taipei (TW)

(73) Assignee: NATIONAL TAIWAN UNIVERSITY HOSPITAL JINSHAN BRANCH, New Taipei (TW)

(*) Notice: Subject to any disclaimer, the term of this patent is extended or adjusted under 35 U.S.C. 154(b) by 123 days.

(21) Appl. No.: 17/098,938

(22) Filed: Nov. 16, 2020

(65) Prior Publication Data
US 2021/0186707 A1    Jun. 24, 2021

(30) Foreign Application Priority Data
Dec. 19, 2019  (TW) ................................. 108216960

(51) Int. Cl.
*A61F 2/44*       (2006.01)
*A61F 2/46*       (2006.01)
(Continued)

(52) U.S. Cl.
CPC ............ *A61F 2/447* (2013.01); *A61F 2/2846* (2013.01); *A61F 2002/30164* (2013.01);
(Continued)

(58) Field of Classification Search
CPC .................... A61F 2/447; A61F 2/2846; A61F 2002/30164; A61F 2002/30329; A61F 2002/30471; A61F 2002/30672
(Continued)

(56) References Cited

U.S. PATENT DOCUMENTS 5,571,109 A * 11/1996 Bertagnoli ........... A61B 17/025
606/86 A
6,159,211 A * 12/2000 Boriani ................. A61F 2/4455
606/279

(Continued)

FOREIGN PATENT DOCUMENTS

WO    WO 2020/198161    * 10/2020    ............... A61F 2/44

*Primary Examiner* — Jessica Weiss
(74) *Attorney, Agent, or Firm* — MUNCY, GEISSLER, OLDS & LOWE, P.C.

(57) ABSTRACT

The present invention provides a supporting member and a supporting member assembly including the same to be implanted into or between a subject's bones, and a template plug and a tamper corresponding to the supporting member. The supporting member comprises a main body; a first connecting portion and a second connecting portion formed on the upper and lower sides of the main body respectively and forming a dovetail joint with each other; and a guiding structure formed at a side of the main body and including guiding holes as well as a buffer groove for mating with an external template plug. The supporting members of the invention can be sequentially implanted and connected into a bone or between two connected bones, and improve the defect of the conventional one-size giant implants injuring the surrounding nerves.

14 Claims, 14 Drawing Sheets

(51) Int. Cl.
*A61F 2/28* (2006.01)
*A61F 2/30* (2006.01)

(52) U.S. Cl.
CPC ............ *A61F 2002/30329* (2013.01); *A61F 2002/30471* (2013.01); *A61F 2002/30672* (2013.01)

(58) Field of Classification Search
USPC ................. 623/17.11–17.16; 606/99–100
See application file for complete search history.

(56) References Cited

U.S. PATENT DOCUMENTS

| | | | | |
|---|---|---|---|---|
| 6,595,998 B2 * | 7/2003 | Johnson | ............... | A61F 2/44 606/279 |
| 7,967,867 B2 * | 6/2011 | Barreiro | ............... | A61F 2/4455 623/17.15 |
| 8,663,332 B1 * | 3/2014 | To | ............... | A61F 2/442 623/17.12 |
| 8,900,312 B2 * | 12/2014 | McLean | ............... | A61F 2/442 623/17.16 |
| 2003/0083747 A1 * | 5/2003 | Winterbottom | ............... | A61F 2/4455 623/17.11 |
| 2003/0105528 A1 * | 6/2003 | Shimp | ............... | A61F 2/28 623/901 |
| 2003/0191531 A1 * | 10/2003 | Berry | ............... | A61F 2/4455 623/17.11 |
| 2003/0233145 A1 * | 12/2003 | Landry | ............... | A61F 2/4657 606/100 |
| 2005/0060034 A1 * | 3/2005 | Berry | ............... | A61F 2/44 623/17.14 |
| 2008/0015702 A1 * | 1/2008 | Lakin | ............... | A61F 2/4425 623/17.16 |
| 2011/0045087 A1 * | 2/2011 | Kerr | ............... | C08J 9/26 424/490 |
| 2014/0107788 A1 * | 4/2014 | Barreiro | ............... | A61F 2/442 623/17.16 |
| 2015/0045893 A1 * | 2/2015 | Dinville | ............... | A61F 2/447 623/17.16 |

* cited by examiner (a)

(b)

(a)

(b)

(a)

(b)

(a)

(b)

(a)

(b)

(a)

(b)

(a)

(b)

(a)

(b)

SUPPORTING MEMBER AND SUPPORTING MEMBER ASSEMBLY FOR IMPLANTATION INTO OR BETWEEN SUBJECTS BONES, AND TEMPLATE PLUG AND TAMPER CORRESPONDING TO THE SAME

BACKGROUND OF THE INVENTION

1. Technical Field

The present invention relates to a supporting member and a supporting member assembly to be implanted into or between a subject's bones, and an insertion tool and a tamper corresponding to the supporting member. More particularly, the invention relates to a supporting member that can be connected with at least one supporting member of the same structure as its own in a bone or between two connected bones, a supporting member assembly composed of such supporting members, and an insertion tool and a tamper corresponding to such supporting members.

2. Description of Related Art

The societies many of us live in are aging or aged, which raises concerns about health issues of the elderly. A senior citizen tends to suffer from osteoporosis and is therefore prone to bone fractures or even vertebral compression fractures. While vertebral compression fractures in most patients can heal within months, the recovery period is anything but easy. For example, persistent pain in the lower back or nerve compression may inconvenience a patient's daily life to such an extent that the patient ends up bedridden, whose complications include bedsores, pneumonia, and urinary infection, among others. Some patients' vertebral compression fractures do not heal at all and hence give rise to permanent pain, if not compromising the stability of the entire vertebral column or leading to a hunchback, in the latter case of which the vertebrae adjacent to the fractured one(s) may suffer from compression fracture too, as in a domino effect. Besides, patients with such related diseases as degenerative disc disease, herniation of intervertebral disc, spondylolisthesis, spondylolysis, spinal canal stenosis, or pseudoarthrosis may experience back pain, sciatica, claudication, or weakness in the legs.

Treatment for vertebral compression fracture can be carried out in many ways. "Open posterior spinal fixation" and "bone fusion surgery" involve driving pedicle screws into fractured vertebrae in order to secure and support the vertebrae. "Minimally invasive percutaneous vertebroplasty" is an X-ray image-guided procedure in which a bone puncture needle injects bone cement into a collapsed fractured vertebra through a tiny incision and a pedicle of the vertebra in order to fill the vertebra with bone cement and thereby relieve pain, but this procedure cannot correct a deformed vertebra. "Minimally invasive percutaneous balloon kyphoplasty" uses an inflatable balloon to restore the height of a collapsed vertebra and, after removal of the balloon, injects bone cement into the cavity formed by the inflated balloon in order to correct the deformation of the collapsed vertebra to a certain degree. This procedure, however, is not very effective in correcting a deformed vertebra and requires bone cement, too. Other treatments include implanting a high-precision medical device (e.g., one designed on the mechanical principle of a jack or tripod) into a fractured vertebra for support, and yet such medical devices are disadvantaged by their complicated mechanical structures, limited supporting effect, and the necessity of filling with bone cement on a supplementary basis.

Another method for treating a vertebral compression fracture entails placing an implant into the fractured vertebra. However, an overly large implant may rupture the pedicle through which it passes during implantation, causing damage to the nearby nerves, and an implant that is not large enough for the intended collapsed vertebra can only expand the vertebra to a limited extent and therefore fails to support the vertebra adequately.

As to treatment between a subject's bones, or interosseous treatment, it is common practice nowadays to incorporate "intervertebral fusion" with "posterior spinal instrumentation" to enhance the effect of rigid fixation.

Intervertebral fusion can be divided by its approach into: anterior lumbar interbody fusion (ALIF), lateral/oblique lumbar interbody fusion (LLIF/OLIF), and posterolateral/transforaminal lumbar interbody fusion (PLIF/TLIF). ALIF is the golden rule in the art, allowing the largest possible support element to be implanted, but is disadvantageous in that it is performed by way of the abdominal cavity, requires a relatively large incision, and may injure the intestinal tract, the abdominal aorta, or the ureters, if not resulting in hernia or retrograde ejaculation at the same time. Technically, therefore, ALIF is highly demanding on both orthopedic and neurological surgeons. LLIF/OLIF reduces the disadvantages of ALIF but necessitates special equipment. PLIF/TLIF is clinically the most widely used, and yet the limited window attributable to obstruction by the spinal cord and the spinal nerves makes it difficult to use an adequately sized support element.

Currently, intervertebral fusion can be assisted by placing an implant between the vertebrae to be fused. However, an exceedingly large implant may injure the surrounding nerves, blood vessels, or other important tissues during implantation, and an implant whose size is smaller than required may result in overly small areas of contact with the adjacent vertebrae, causing problems associated with undue concentration of pressure.

BRIEF SUMMARY OF THE INVENTION

With regard to implantation into a subject's bones, the conventional open posterior spinal fixation and bone fusion procedure when performed on a patient with osteoporosis may require a relatively large incision and use a relatively large number of screws to secure a relatively large number of vertebrae in order to prevent the screws from getting loose. Nevertheless, an extensive spinal fixation operation not only is time-consuming and prone to massive blood loss, but also may lead to the development of multiple complications (e.g., stiffness in the back, cardiopulmonary failure, and infection) in elderly patients. As to minimally invasive percutaneous vertebroplasty or kyphoplasty, the bone cement used in the operation may leak from the vertebra(e) in question, and a serious leak into blood vessels may result in arterial thrombosis, venous thrombosis, or stroke. If a lot of bone cement leaks to the spinal cord or the nerve roots and subsequently cures (the curing process generates high heat), the surrounding nerves will be severely compressed and damaged. Moreover, when bone cement exists permanently as the filler in a fractured vertebra, the low bone-compatibility and extremely high hardness of bone cement may give rise to bone resorption, hinder the healing of the fracture, or even fracture a neighboring vertebra.

As for implantation between a subject's bones, the conventional devices for intervertebral fusion are the intervertebral cages, which can be roughly divided into those of a unitary structure and those of a composite structure. Common unitary-structure cages are in the shape of a disc, straight bullet, or banana and have a simple structural design that requires the use of a complicated tool during implantation in order to prevent nerve and blood vessel injuries. Clinically, therefore, a unitary-structure intervertebral cage often falls short of its required dimensions such that the areas of contact between the cage and the adjacent vertebrae are not large enough to avoid pressure concentration (which may cause subsidence or extrusion of the intervertebral cage into or from the vertebrae) or promote intervertebral fusion (the failure of which may lead to the formation of a false joint, i.e., pseudoarthrosis). Composite-structure intervertebral cages either incorporate a screw or have an expandable structure. The screw-type cages, though featuring enhanced fixation, add to the difficulty of surgical operation and are applicable only in ALIF. The expandable-structure intervertebral cages can be further divided into the medial-lateral expansion type and the caudal-cranial expansion type, both of which enable relatively large areas of contact and increased fixation but have rather intricate mechanical structures, including, for example, a large number of articulations and points of stress concentration. These complex structures not only limit the amount of bone graft that can be packaged in each cage, but also increase the chances of long-term fatigue failure and false joint formation between vertebrae.

As is well known in the art, a bone implant must not be a complicated mechanical assembly, which tends to fatigue, disintegrate, or fail after persistent use in the human body. In addition, a bone implant is preferably highly bone-compatible or even conducive to the healing of bone fracture and therefore must not include materials that are rarely used, or not allowed to be used, in the human body. Regarding the treatment of bone fracture, therefore, many issues remain to be addressed by medical experts and scientific researchers.

In view of this, in order to solve the above problems, the primary objective of the present invention is to provide a supporting member for implantation into or between a subject's bones, comprising: a main body having two opposite sides defined respectively as an upper side and a lower side; a first connecting portion formed at the upper side of the main body and shaped as a male or female part of a dovetail joint; a second connecting portion formed at the lower side of the main body and corresponding in shape to the first connecting portion; and a guiding structure formed at a side of the main body and configured to mate with an insertion tool; wherein the first connecting portion of the supporting member is connectable with the second connecting portion of another said supporting member to form a said dovetail joint.

In a preferred embodiment, the first connecting portion is a dovetail block and the second connecting portion is a dovetail groove in order to prevent two vertically connected said supporting members from separating from each other after connecting in a sliding manner.

In a preferred embodiment, a front side of the first connecting portion further includes a first positioning portion, a front side of the second connecting portion further includes a second positioning portion, and the second positioning portion corresponds in shape and position to the first positioning portion; wherein, the first positioning portion is a positioning block and the second positioning portion is a positioning hole so that the supporting members with such structures are able to position and fasten to each other.

In a preferred embodiment, a front side of the main body has a U-shaped groove structure that can be compressed or deformed to facilitate fastening between supporting members and return to an original shape elastically to prevent the supporting members from separating from each other.

In a preferred embodiment, the guiding structure includes a plurality of guiding holes and/or buffer grooves.

In a preferred embodiment, the guiding holes and the buffer grooves have various designs with progressive deviation or difference in terms of angle, position, size, or shape.

In a preferred embodiment, the main body is one or a plurality of reticulated structures.

In a preferred embodiment, the reticulated structure can be filled with a bone-filling material or bone cement.

In a preferred embodiment, the bone is a vertebra.

In a preferred embodiment, a material of the supporting member includes metal, plastic, or a mixture thereof.

Another objective of the present invention is to provide an insertion tool configured to guide the aforementioned supporting member into or between a subject's bones, which includes a plurality of connecting pins, an extension portion, and a grip portion, wherein the extension portion has one end connected to the plural connecting pins and an opposite end connected to the grip portion, and the extension portion and/or the grip portion has: a third connecting portion, which is formed on an upper side of the extension portion and/or the grip portion, and is a dovetail projection; a fourth connecting portion, which is formed on a lower side of the extension portion and/or the grip portion, and corresponds to the third connecting portion; wherein, the plural connecting pins can be correspondingly engaged with the guiding structure of the supporting member.

In a preferred embodiment, the insertion tool further includes a plurality of connecting pins and buffer bases.

In a preferred embodiment, the insertion tool has two connecting pins that correspond in design to but are slightly different from the guiding structure in terms of angle, position, shape, or size.

In a preferred embodiment, the third connecting portion of the insertion tool can correspond to the second connecting portion of the supporting member and the fourth connecting portion can correspond to the first connecting portion of the supporting member so that the insertion tool can be pushed along and coupled with the supporting member in a sliding manner.

Still another objective of the present invention is to provide a tamper, which can correspondingly match the aforementioned supporting member or insertion tool, the tamper includes a slender shaft and a grip portion connected to the slender shaft; wherein, an upper side of the slender shaft and/or the grip portion further includes a fifth connecting portion corresponding to the second connecting portion, and a lower side of the slender shaft and/or the grip portion further includes a sixth connecting portion corresponding to the first connecting portion.

Yet another objective of the present invention is to provide a supporting member assembly to be implanted into or between a subject's bones, which includes a plurality of aforementioned supporting members, wherein the first connecting portion of each supporting member forms a dovetail joint with the second connecting portion of another said supporting member in order to connect the plural supporting members sequentially.

The present invention has the following advantages:

1. The present invention provides a supporting member that is configured as a micro-unit and whose small size allows not only implantation into a bone or between two connected bones, but also connection with other such members in the bone or between the connected bones so as to form a supporting member assembly, making possible a minimally invasive, small-incision surgical operation.

2. The present invention also provides a tamper for restoring a fractured bone and pushing/pressing an implanted supporting member, and an insertion tool for introducing a supporting member into a bone or between two connected bones, connecting the supporting member to a previously implanted supporting member in a sliding manner, and thereby fastening the two supporting members together vertically, before the insertion tool is removed from the supporting members.

3. The present invention further provides a supporting member assembly that is formed by sequentially implanting and connecting a plurality of supporting members into a bone or between two connected bones so as to push outward the end plate(s) to be treated and thereby expand the collapsed fractured bone(s). This supporting member assembly is an improvement over the one-size implants used in the conventional implantation techniques on the grounds that an existing one-size implant cannot "be a single micro-unit before implantation into or between a subject's bones and connect with other similar micro-units sequentially implanted into or between the bones to form a larger yet complete block". In addition, unlike the traditional one-size implants, the supporting member assembly of the invention will not rupture the affected bone structure (e.g., a pedicle) or injure the surrounding nerves (e.g., the spinal cord or spinal nerves), blood vessels (e.g., the abdominal aorta or the vertebral arteries), or other important tissues (e.g., the ureters) during implantation, or provide inadequate support due to an expediently smaller-than-required size.

DETAILED DESCRIPTION OF THE INVENTION

Figure 1:
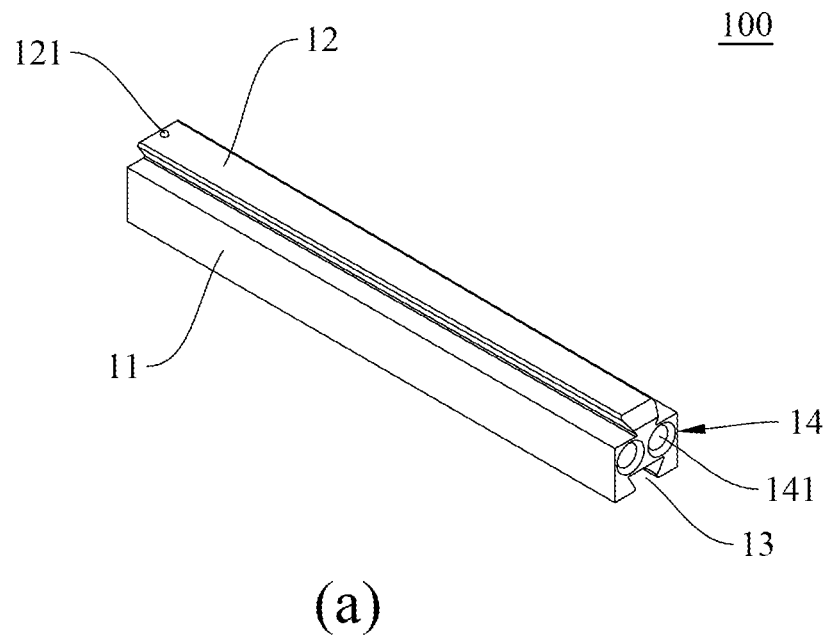
FIGS. 1 (*a*) and (*b*) show perspective views of the supporting member according to embodiment 1 of the present invention.
Figure 1:
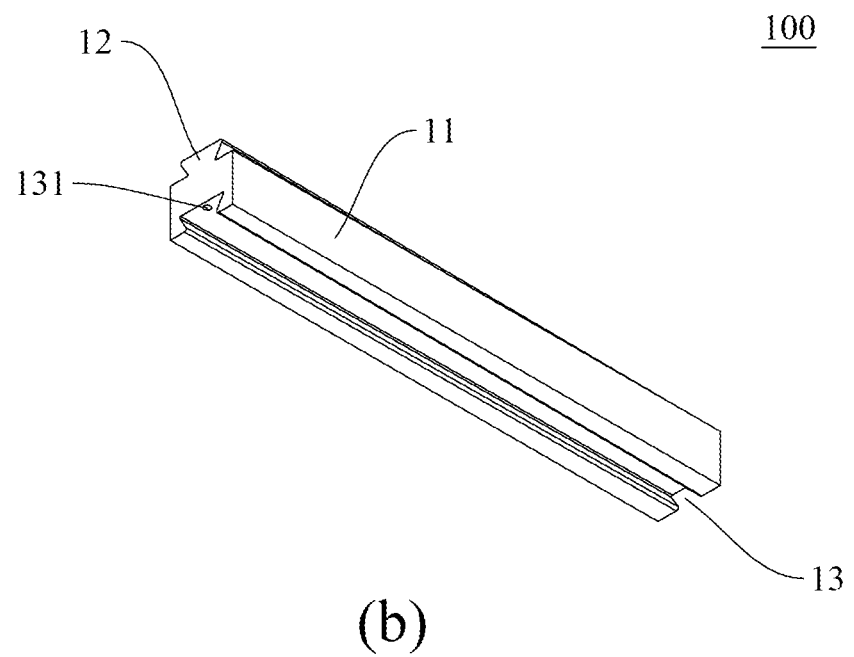

The details and technical solution of the present invention are hereunder described with reference to accompanying drawings. For illustrative sake, the accompanying drawings are not drawn to scale. The accompanying drawings and the scale thereof are not restrictive of the present invention.

The use of "comprise/include" means not excluding the presence or addition of one or more other components, steps, operations, and/or elements to the described components, steps, operations, and/or elements. As used herein and in the appended claims, the singular forms "a," "an," and "the" include plural referents unless the context dictates otherwise.

Hereinafter, the present invention will be further described with detailed descriptions and embodiments. However, it should be understood that these embodiments are only used to help understand the invention more easily, not to limit the scope of the invention.

The present invention is designed not only for implantation into or between human bones, but also for use in other vertebrates such as amphibians, reptiles, birds, and mammals. Furthermore, the invention can be used in or between any suitable bones, preferably but not limited to vertebrae. In one preferred embodiment, the bone to which the invention is applied is a vertebra.

Generally speaking, a conventional bone implant cannot be minimally invasive and adequately supportive at the same time. To solve the clinical problems associated with bone fracture effectively, the present invention aims to provide a supporting member, a supporting member assembly, an insertion tool for guiding the supporting member into a subject's bone or between two connected bones, and a tamper for assisting the required implantation operation. A detailed description of some embodiments of the invention is given below.

[Embodiments 1 to 4]—Supporting Member

Please refer to FIG. 1 to FIG. 4 for perspective views of four supporting members 100 according respectively to embodiments 1 to 4 of the present invention.

The supporting members 100 according to embodiments 1 to 4 are configured to be implanted into or between a subject's bones and each include a main body 11, a first connecting portion 12, a second connecting portion 13, and a guiding structure 14. The main body 11 has an upper side and a lower side, which is the opposite side of the upper side. In embodiment 3, referring to FIG. 3, the main body 11 is preferably one or a plurality of reticulated structures. This embodiment is advantageous in that the at least one reticulated structure can be filled with a bone-filling material (e.g., bone cement), provides space for the proliferation of osteoblasts, allows passage of nutrients, produces a supporting effect similar to that of trabeculae, and facilitates fusion between the main body of the supporting member (or the filler therein) and the surrounding ossein, thereby assisting in the healing of a bone fracture. In embodiment 2, referring to FIG. 2, the main body 11 has one or a plurality of holes (e.g., through holes with a diameter ranging from about 0.3 mm to about 5 mm), wherein the at least one hole is intended to provide space that can be filled with a bone-filling material, promote the proliferation of osteoblasts and the delivery of nutrients, enhance filler (e.g., bone cement) attachment, and reduce the weight and Young's modulus (also known as the modulus of elasticity) of the implant.

Figure 5:
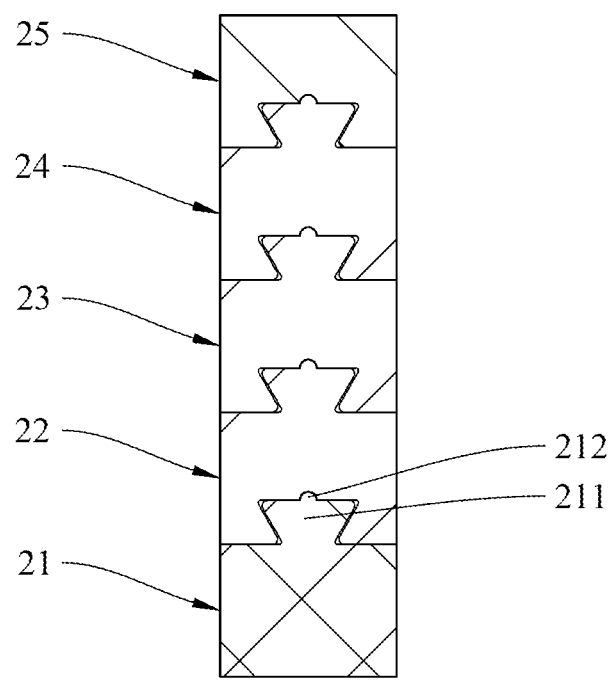
FIG. 5 is a sectional view of the supporting member assembly according to a preferred embodiment of the present invention.

The first connecting portion 12 is formed on the upper side of the main body 11 and is shaped as the male part of a dovetail joint. The second connecting portion 13 is formed in the lower side of the main body 11 and corresponds in shape to the first connecting portion 12. The first connecting portion 12 of a supporting member 100 can be connected to the second connecting portion 13 of another supporting member 100 to form a dovetail joint. As used herein, the term "male (or female) part of a dovetail joint" refers to a trapezoidal structure protruding from (or sunken into) the main body 11, and the term "dovetail joint" refers to a joint formed by such a protruding trapezoidal structure engaged with, fastened to, connected in a sliding manner to, or otherwise secured in a matching sunken trapezoidal structure. In one preferred embodiment, the first connecting portion is a dovetail block, the second connecting portion is a dovetail groove, and the first connecting portion of a supporting member with such connecting portions can form a dovetail joint with the second connecting portion of another such supporting member, as shown in FIG. 5. This structural feature aims to prevent two vertically connected supporting members from tilting sideways with respect to and separating vertically from each other after the trapezoidal dovetail groove of the upper supporting member is mated, in a sliding manner, to the "top rail" formed by the dovetail block of the lower supporting member; in short, the structural feature is intended to fasten or lock the supporting members together after the supporting members are implanted into a bone or between two connected bones. In some embodiments, the first connecting portion is a dovetail block whose width gradually increases from the front end toward the rear end, and the second connecting portion has a corresponding shape so that while the second connecting portion of a supporting member with such connecting portions is being mated, in a sliding manner, to the dovetail block of another such supporting member, the former supporting member can only be moved forward but not rearward.

Figure 2:
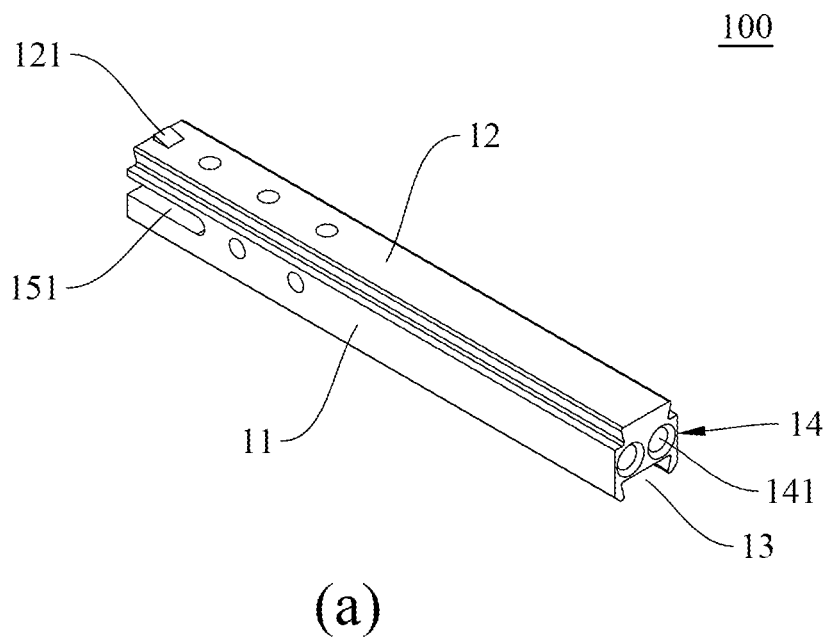
FIGS. 2 (*a*) and (*b*) show perspective views of the supporting member according to embodiment 2 of the present invention.
Figure 2:
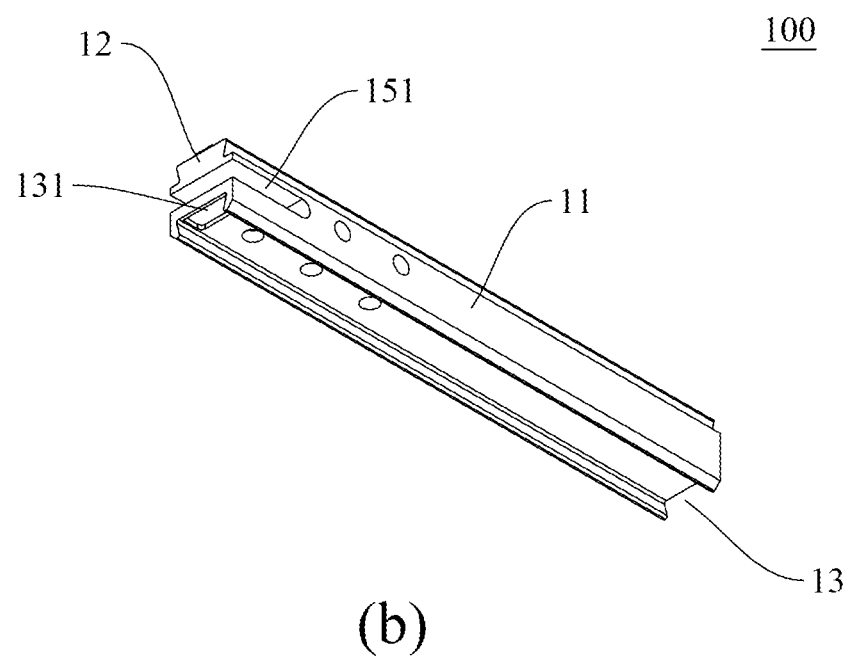
Figure 3:
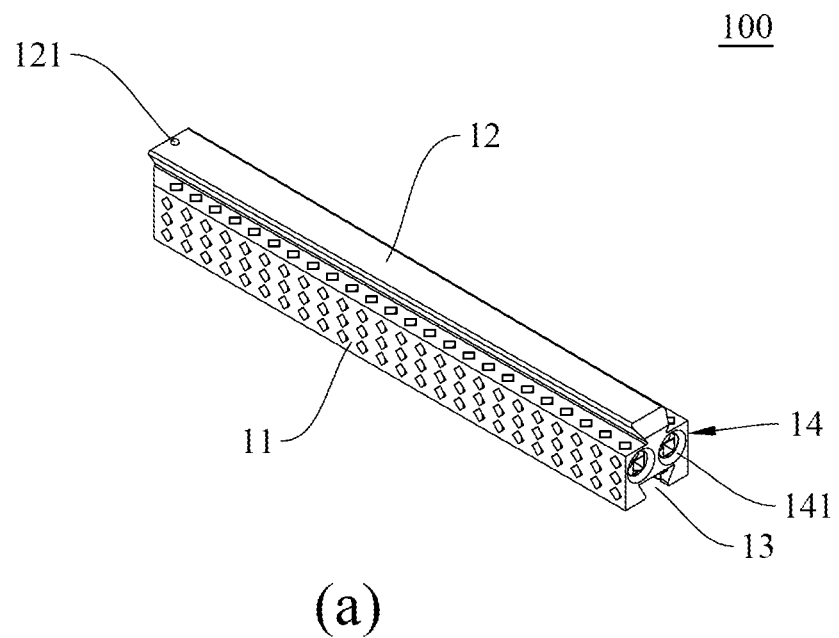
FIGS. 3 (*a*) and (*b*) show perspective views of the supporting member according to embodiment 3 of the present invention.
Figure 3:
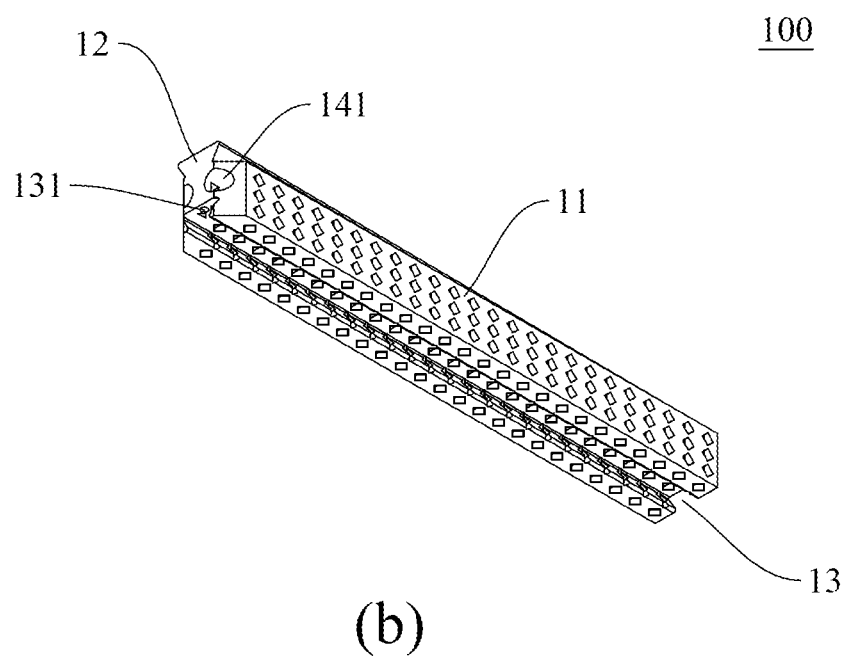
Figure 4:
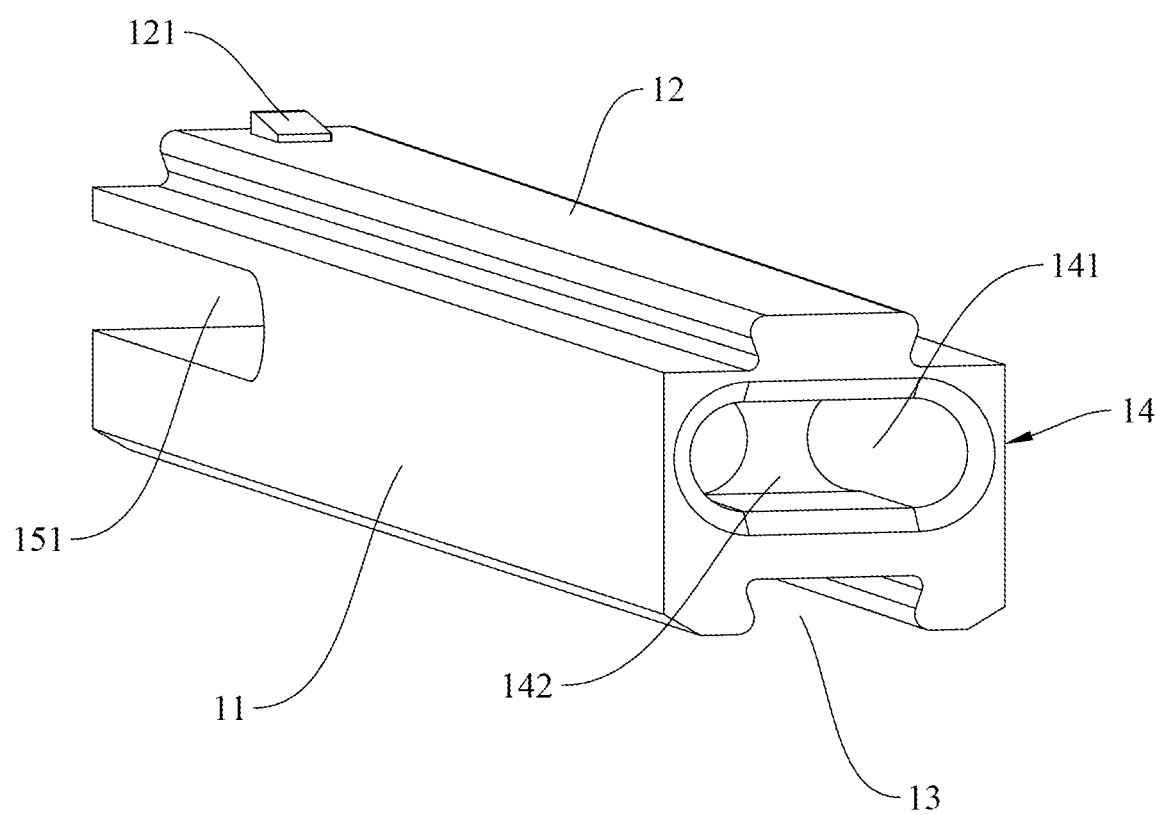
FIG. 4 is a perspective view of the supporting member according to embodiment 4 of the present invention.

In some embodiments, the first connecting portion further includes a first positioning portion, and the second connecting portion further includes a second positioning portion corresponding in shape and position to the first positioning portion. For example, the first positioning portion may be a protruding structure while the second positioning portion is a recessed structure corresponding in shape to the protruding structure, or the first positioning portion may be a recessed structure while the second positioning portion is a protruding structure corresponding in shape to the recessed structure. The foregoing designs of the positioning portions are advantageous in that the first positioning portion and the second positioning portion can be fastened to each other to prevent two connected supporting members from getting loose with respect to each other. In one preferred embodiment, the first positioning portion is a projection, and the second positioning portion is a recess. In embodiment 3 as well as embodiment 1, the front side of the first connecting portion 12 of the supporting member 100 is provided with a terminal positioning bump (i.e., the first positioning portion 121), and the bump can enter, in a sliding manner, a positioning hole (i.e., the second positioning portion 131) of the next implanted supporting member 100 to prevent the two supporting members 100 from sliding with respect to and separating from each other in either the forward or the rearward direction. In embodiment 4 as well as embodiment 2, the front side of the first connecting portion 12 of the supporting member 100 is provided with a terminal positioning block (i.e., the first positioning portion 121), and the block can enter, in a sliding manner, a positioning groove (i.e., the second positioning portion 131) of the next implanted supporting member 100 to prevent the two supporting members 100 from sliding with respect to and separating from each other in either the forward or the rearward direction. In one preferred embodiment, the main body 11 has a U-shaped groove structure 151 as shown in FIG. 2 and FIG. 4 so that when a supporting member with such a structure is brought into engagement with another such supporting member in a sliding manner, and before their positioning portions (e.g., a positioning bump and a positioning hole) are fastened to each other, the U-shaped groove structures 151 of the two supporting members can be elastically compressed or deformed to facilitate fastening between the positioning bump and the positioning hole, and that after the positioning portions are fastened together, the U-shaped groove structures 151 will return to their original shapes elastically to ensure that the positioning bump is securely fastened to the positioning hole to prevent the supporting members from separating from each other.

The guiding structure 14 is formed at one side of the main body 11 and is configured to mate with an insertion tool. The guiding structure 14 may be, for example but not limited to, the guiding holes 141 shown in FIG. 1 to FIG. 4. In one preferred embodiment, the guiding structure 14 includes a plurality of guiding holes (such as but not limited to two, three, four, or five guiding holes), and there is no limitation on the shapes of the guiding holes (e.g., the guiding holes may be circular holes, rectangular holes, triangular holes, other polygonal holes, or holes of irregular shapes). In each of embodiments 1 to 3, the main body 11 is formed at one side with two guiding holes 141 for mating with an insertion tool. In embodiment 4, referring to FIG. 4, there are also two guiding holes 141, but the guiding holes 141 are connected by a gradually deepened buffer groove 142 that is relatively wide at a shallow depth and turns pointed as the depth increases. These two guiding holes 141 and the buffer groove 142 between them are also designed to mate with an insertion tool. The guiding structure 14 aims to connect with the "connecting pins" at the front end of an insertion tool (as detailed further below). The two guiding holes 141 and the buffer groove 142 in embodiment 4 may have various designs in terms of angle (e.g., they may diverge or converge in the forward direction), position (e.g., they may be shifted laterally outward or inward with respect to one another), size (e.g., they may be tapered in the forward or rearward direction), or shape (e.g., they may be conical or columnar).

In one preferred embodiment, the material of the supporting member of the present invention includes a biocompatible material such as a biocompatible metal, a biocompatible plastic, or a mixture thereof. Suitable metals include but are not limited to magnesium alloys, tantalum alloys (e.g., TaC and TaN), titanium alloys (e.g., GUMMETAL®), nickel-titanium alloys, nickel-titanium-copper alloys, cobalt-chromium alloys (e.g., Elgiloy®, a non-magnetic cobalt-based hardenable cobalt-chromium-nickel superalloy), cobaltchromium-nickel alloys (e.g., Phynox®), chromium-tungsten-nickel alloys (e.g., L605), cobalt-chromium-vanadium alloys, cobalt-nickel-chromium-molybdenum alloys (e.g., MP35N and MP20N), stainless steel (e.g., 316, 316L, and 304), and metallic glass. Suitable plastics include polymers, copolymers, composite materials, and mixtures of the above, such as but not limited to styrene-based elastomers, olefinic elastomers, polyolefinic elastomers, polyurethane-based thermoplastic elastomers, polyamides, polybutadienes, polyisobutylene, poly(styrene-butadiene-styrene), poly(2-chloro-1,3-butadiene), silicones, thermoplastic polyurethanes (TPU), polyurethanes (PU), polysiloxanes (e.g., polydimethylsiloxane (PDMS) and hard polydimethylsiloxane (h-PDMS)), poly(methyl methacrylate) (PMMA), polyetheretherketone (PEEK), ultra-high-molecular-weight polyethylenes (UHMWPE), and silicon rubber. In a more preferred embodiment, the material of the supporting member of the invention includes a titanium alloy. The foregoing embodiments are advantageous in that a plurality of supporting members may, depending on their material properties, be sequentially implanted into a bone or between two connected bones, fastened together, and vertically or horizontally stacked until the resulting supporting member assembly has the desired height/width and supporting strength.

The dimensions of the supporting member of the present invention are preferably determined according to the size of the space of the target implantation site and the size of the incision to be made for the implantation operation. For example, if the target implantation site is in a vertebra, the supporting member may have a relatively slender design to minimize the hole drilled into the vertebra and thereby protect the surrounding nerves and blood vessels from injury. That is to say, the supporting member of the invention can be adjusted and modified as needed. The invention imposes no limitation on the dimensions of the supporting member.

[Embodiment 5]—Supporting Member Assembly

Figure 6:
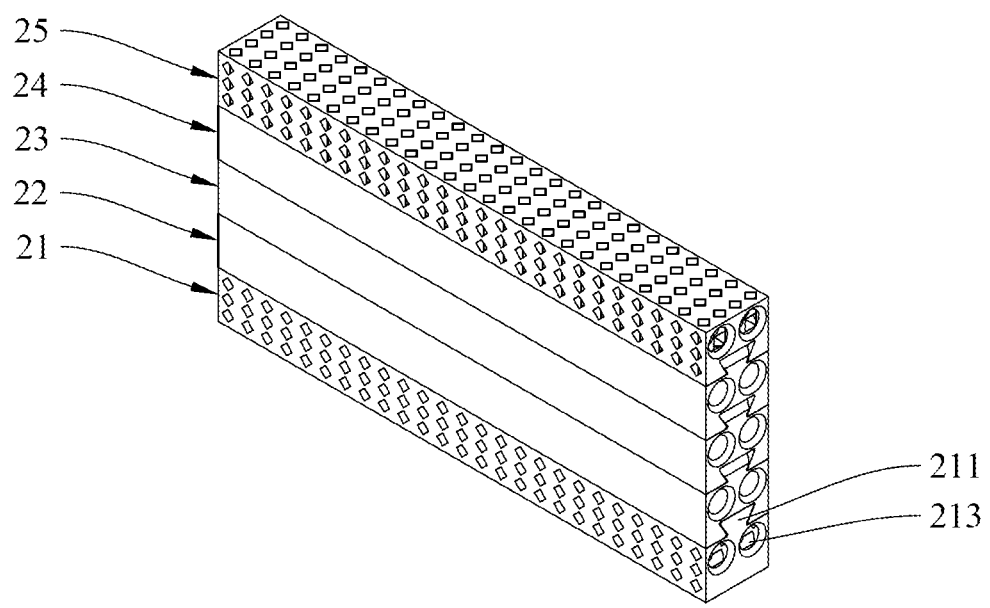
FIG. 6 is a perspective view of the supporting member assembly according to embodiment 5 of the present invention.

Please refer to FIG. 5 and FIG. 6 respectively for a sectional view and a perspective view of the supporting member assembly 200 according to embodiment 5 of the present invention. The supporting members in the supporting member assembly 200 are sequentially identified in a bottom-up order as the first supporting member 21, the second supporting member 22, the third supporting member 23, the fourth supporting member 24, and the fifth supporting member 25. As the supporting members are implanted in the same direction, their guiding structures 213 face the same direction.

The supporting member assembly 200 according to embodiment 5 is configured to be implanted into or between a subject's bones and includes the plural supporting members stated above, with the first connecting portion of each supporting member (except for the uppermost supporting member 25) forming a dovetail joint with the second connecting portion of the adjacent supporting member. As shown in FIG. 5, the plural supporting members are sequentially connected in such a way that the first connecting portion (i.e., the connecting portion 211) of each supporting member (except for the uppermost supporting member 25) forms a dovetail joint with the second connecting portion of the next implanted supporting member. During the process, the first positioning portion (i.e., the positioning portion 212) of each supporting member (except for the uppermost supporting member 25) is slid into the second positioning portion of the next implanted supporting member to prevent each two adjacent supporting members from sliding with respect to each other in the forward or rearward direction.

In one preferred embodiment, the supporting member assembly includes two to seven supporting members. In a more preferred embodiment, the supporting member assembly includes three to five supporting members. In the embodiment shown in FIG. 5 and FIG. 6, the supporting member assembly 200 is an assembly of five supporting members, in which, as shown in FIG. 6, the first supporting member 21 and the fifth supporting member 25 are reticulated structures to provide the space needed for the proliferation of osteoblasts and allow passage of nutrients, and in which the second to the fourth supporting members 22, 23 and 24 are solid structures to be stacked up to increase the height of the space created by the assembly as well as the strength of the assembly, with a view to, for example, pushing two adjacent vertebrae further apart from each other vertically. It can also be seen in FIG. 5 and FIG. 6 that the first supporting member 21, which only has to connect with the second supporting member 22, may have only the first connecting portion, and that the fifth supporting member 25, which only has to connect with the fourth supporting member 24, may have only the second connecting portion.

A plurality of supporting members of the present invention can be fastened together in a modular manner while being implanted into a bone or between two connected bones so as to form a vertical or horizontal stack of the desired height or width and with the desired supporting strength. The resulting supporting member assembly can push outward the end plate(s) to be treated, thereby expanding a fractured bone or providing interosseous fixation. The invention allows a plurality of supporting members to be connected in the tiny limited space in a bone or between two connected bones in order to stabilize the bone or firmly secure the connected bones. The number of the supporting members required to be implanted depends on the height of the bone to be restored or the distance between the two connected bones to be secured. Theoretically, the supporting member assembly can be made larger by adding as many supporting members as needed, until the bone to be restored or the space between the two connected bones to be secured is completely filled by the assembly. Thus, the invention overcomes the aforementioned drawback of the conventional one-size implants, i.e., failure to "be a single micro-unit before implantation into or between a subject's bones and connect with other similar micro-units sequentially implanted into or between the bones to form a larger yet complete block". The invention also solves such problems of the conventional one-size implants as the likelihood of their rupturing the affected bone structure (e.g., a pedicle) or injuring the surrounding nerves (e.g., the spinal cord or spinal nerves), blood vessels (e.g., the abdominal aorta or the vertebral arteries), or other important tissues (e.g., the ureters) during implantation, and of their providing inadequate support due to an expediently smaller-than-required size.

To put together a plurality of supporting members of the present invention, two insertion tools according to the invention can be sequentially mated to the guiding structures of the supporting members in order to guide each supporting member into a subject's bone or between two connected bones, connect each two successively implanted supporting members in a sliding manner, and fasten each two successively implanted supporting members together vertically. During the process, each insertion tool is removed from the supporting member it is mated to, after the other insertion tool has put the next supporting member in place. The implantation and connection process are detailed below with reference to FIG. 7.

The supporting members 311 of the present invention are configured to work with a working assembly in order to be implanted. The supporting members 311 and the working assembly are herein referred to collectively as an implantation system 300.

The working assembly matches the supporting members 311 and is configured to implant the supporting members 311 into or between a subject's bones. The working assembly includes one or a combination of devices selected from the group consisting of an introducer (not shown), a reamer (not shown), a working cannula 33, a tamper (not shown), and an insertion tool 32.

The introducer includes an introducing portion, an extension portion, and a grip portion. The extension portion has one end connected to the introducing portion and the opposite end connected to the grip portion. The end of the introducing portion that is not connected to the extension portion is pointed and sharp. In one preferred embodiment, the introducing portion and the extension portion of the introducer may be solid or hollow. The introducer is configured to make a hole into a vertebra and gradually enlarge the hole so that the working cannula can be put into the hole. In fact, the introducer refers to any one of a series of solid or hollow introducers that have a needle-shaped introducing portion and vary in size so as to drill and enlarge a hole in a vertebra in a successive and gradual manner, lest a large hole drilled into the vertebra in one go injure the surrounding nerves or blood vessels.

The reamer includes a reaming portion, an extension portion, and a grip portion. The extension portion has one end connected to the reaming portion and the opposite end connected to the grip portion. The reaming portion is a sharp spiral structure with which the reamer can move or pull out bone debris. The sharp spiral structure of the reamer can be driven to a specific position in a bone and ream out bone debris for physiological examination.

The working cannula 33 includes a hollow tube and a grip portion. The hollow tube allows insertion by the introducing portion and the extension portion of the introducer, the slender shaft of the tamper, and the two connecting pins and the extension portion of the insertion tool 32. The hollow tubular structure of the working cannula 33 not only can accommodate the largest of the introducers used to gradually enlarge the hole drilled into a vertebra, but also serves as a passage for the reamer, the tamper, the insertion tool 32, and the supporting members 311 to be implanted, thereby limiting the working position of the implantation system 300.

Figure 7:
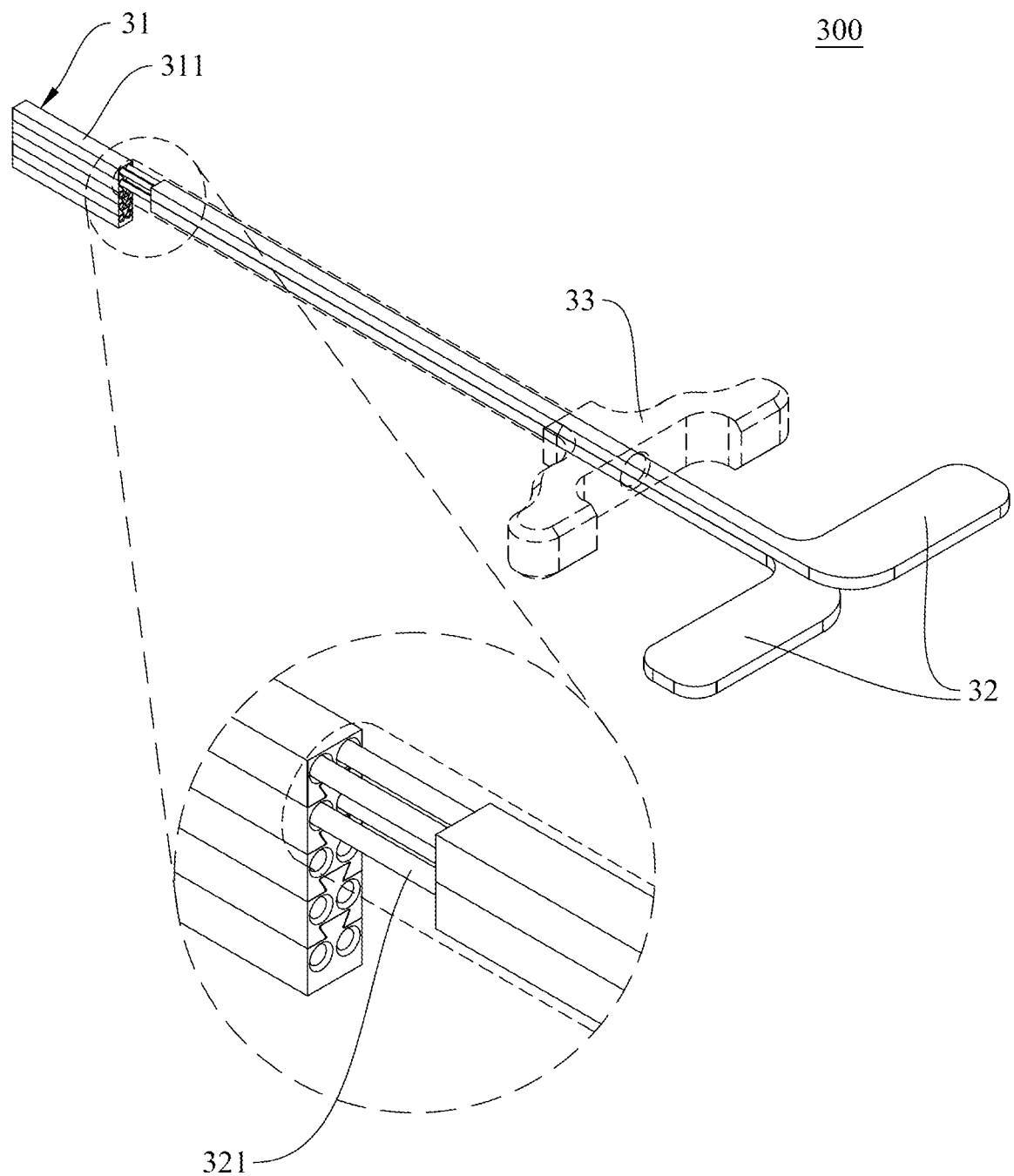
FIG. 7 is a schematic diagram illustrating a preferred embodiment of the implantation system of the present invention.

Some examples of the tamper and of the insertion tool 32 will be detailed below with reference to embodiments 6 to 8. FIG. 7 shows how the supporting members 311 are put together using two insertion tools 32 and how the connecting pins 321 of each insertion tool 32 are mated to the guiding structure of the corresponding supporting member 311. It is feasible to implant only one supporting member 311 into a bone or between two connected bones, or sequentially introduce and connect two or more supporting members 311 into a bone or between two connected bones to form a supporting member assembly 31 with adequate supporting strength.

[Embodiments 6 and 7]—Insertion Tool

Figure 8:
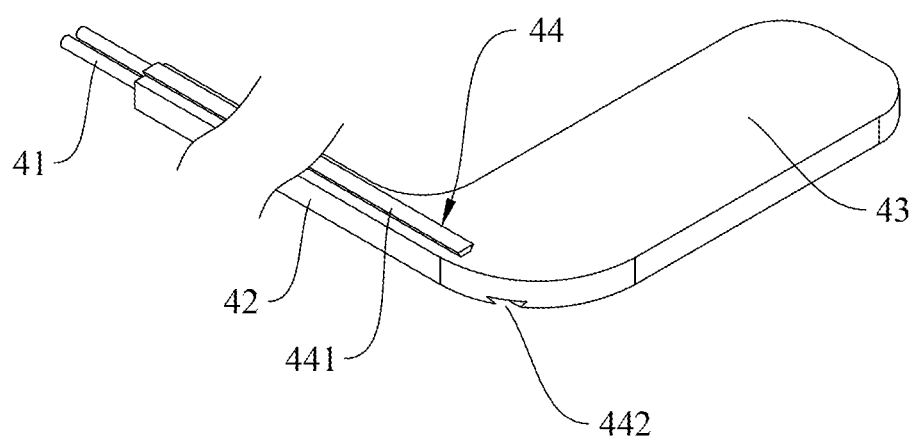
FIGS. 8 (*a*) and (*b*) show perspective views of the insertion tool according to embodiment 6 of the present invention.
Figure 8:
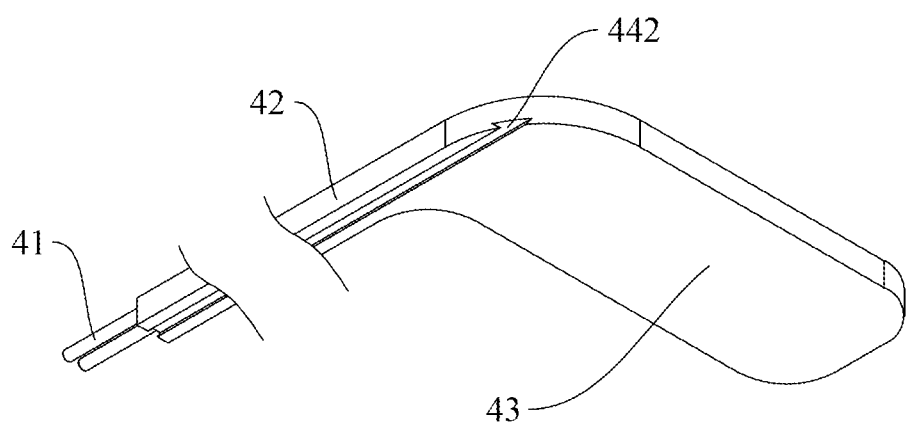
Figure 9:
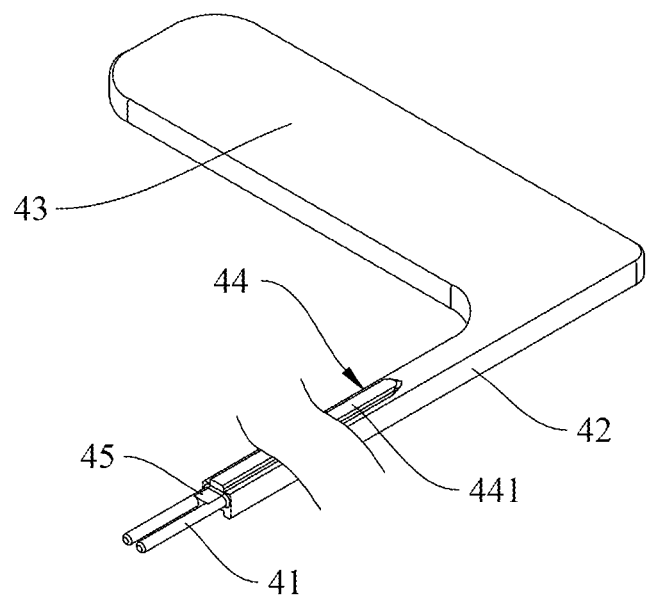
FIGS. 9 (*a*) and (*b*) show perspective views of the insertion tool according to embodiment 7 of the present invention.
Figure 9:
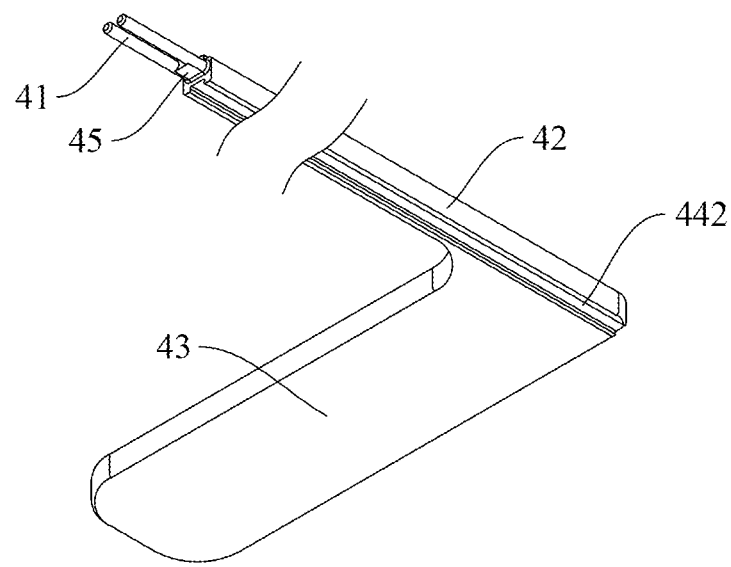

Please refer to FIG. 8 and FIG. 9 for perspective views of two insertion tools 400 according respectively to embodiments 6 and 7 of the present invention.

The insertion tools 400 according to embodiments 6 and 7 are both configured to guide the supporting member of the present invention into or between a subject's bones. Each insertion tool 400 includes a connecting pin 41, an extension portion 42, and a grip portion 43, wherein the extension portion 42 has one end connected to the connecting pin 41 and the opposite end connected to the grip portion 43.

The connecting pin 41 serves to mate with the guiding structure of a supporting member of the present invention and is therefore configured to match the guiding structure in, for example, position, structure, and/or number. As stated above, the guiding structure of a supporting member of the invention may include guiding holes and a buffer groove, both formed in one side of the main body of the supporting member, wherein the number of the guiding holes may be two, three, four, five, etc. It is therefore preferable that there are as many connecting pins as the guiding holes, i.e., two, three, four, or five connecting pins corresponding to two, three, four, or five guiding holes respectively. Take embodiments 1 to 4 for example. The supporting member in each of embodiments 1 to 4 has two guiding holes, and in order to mate with the two guiding holes, the insertion tool 400 in each of embodiments 6 and 7 has two connecting pins 41. In embodiment 7, referring to FIG. 9, the two connecting pins 41 are connected by a gradually raised buffer base 45 that is relatively wide at the rear end and turns pointed toward the front end, and that is intended to correspond to a gradually deepened buffer groove that is relatively wide at a shallow depth and turns pointed as the depth increases. In one preferred embodiment, the two connecting pins correspond in design to but are slightly different from the intended guiding structure in terms of angle (e.g., diverging or converging in the forward direction in the same way as the guiding holes of the guiding structure but to a slightly different degree), position (e.g., shifted laterally outward or inward to a small degree with respect to the guiding holes of the guiding structure), shape (e.g., being conical or columnar in a slightly different way from the guiding holes of the guiding structure), or size (e.g., tapered in the forward or rearward direction to a slightly different degree from the guiding holes of the guiding structure). This structural feature, i.e., the slight structural difference between the connecting pins and the intended guiding structure, aims to enable temporary fastening, and thus temporarily prevent separation, between the insertion tool and each supporting member having the intended guiding structure.

To prevent a plurality of insertion tools 400 that are used together from shifting in position during supporting member implantation, each insertion tool 400 may further include a coupling and positioning structure 44, i.e., a third connecting portion 441 and a fourth connecting portion 442. The third connecting portion 441 is located at an upper side of the extension portion 42 and the grip portion 43, while the fourth connecting portion 442 is located at a lower side of the extension portion 42 and the grip portion 43. For example, the third connecting portion 441 is a dovetail projection corresponding to the dovetail recess, or second connecting portion, of a supporting member of the present invention and can therefore be pushed into, advanced, and coupled with the dovetail recess of the supporting member in a sliding manner, and the fourth connecting portion 442 is a dovetail recess corresponding to the dovetail projection, or first connecting portion, of the supporting member and can therefore be pushed along, advanced, and coupled with the dovetail projection of the supporting member in a sliding manner. As another example, an insertion tool of the invention may have the same upper connecting portion (e.g., dovetail block) and lower connecting portion (e.g., dovetail groove) as a supporting member of the invention so as to connect with another insertion tool of the same configuration.

Referring to FIG. 9, a "first" (with reference to the order of a sequence) insertion tool 400 has its connecting pins 41 and buffer base 45 mated respectively with the guiding holes 141 and the buffer groove 142 of a "first" (with reference to the order of a sequence) supporting member such that the "first" supporting member is held by the "first" insertion tool 400. After the "first" insertion tool 400 puts the "first" supporting member securely into a bone or between two connected bones, the third connecting portion 441 of the "first" insertion tool 400 is coupled to the dovetail recess, or second connecting portion 13, of a "second" (with reference to the order of a sequence) supporting member and to the dovetail recess, or fourth connecting portion 442, of the "second" (with reference to the order of a sequence) insertion tool 400 holding the "second" supporting member. When the "second" insertion tool 400 has fastened the dovetail recess, or second connecting portion 13, of the "second" supporting member to the dovetail projection, or first connecting portion 12, of the "first" supporting member, the "first" insertion tool 400 (or more particularly its connecting pins 41 and buffer base 45) can be removed from the guiding holes 141 and the buffer groove 142 of the "first" supporting member, and by doing so, the third connecting portion 441 of the "first" insertion tool 400 can also be removed from the dovetail recess, or fourth connecting portion 442, of the "second" insertion tool 400.

In short, after the "second" insertion tool holding the "second" supporting member is moved along the "first" insertion tool and fastens the "second" supporting member to the "first" supporting member, the "first" insertion tool can be removed from the "second" insertion tool. By the same token, more than two supporting members can be sequentially introduced into and connected in a bone or between two connected bones.

[Embodiment 8]—Tamper

Figure 10:
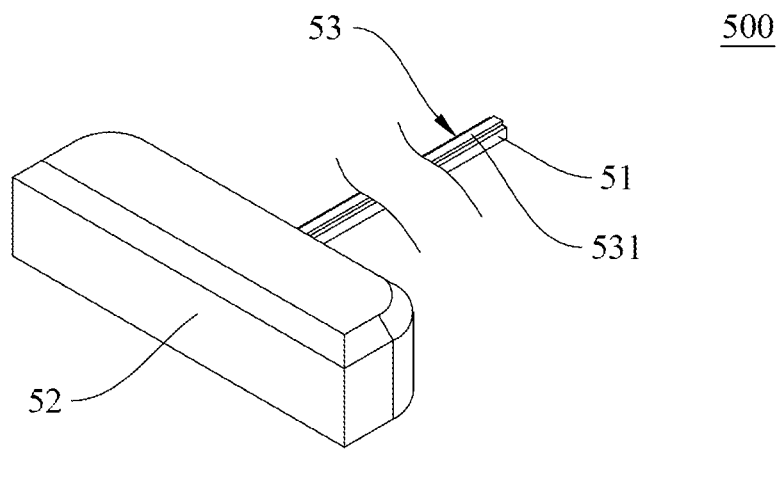
FIGS. 10 (*a*) and (*b*) show perspective views of the tamper according to embodiment 8 of the present invention.
Figure 10:
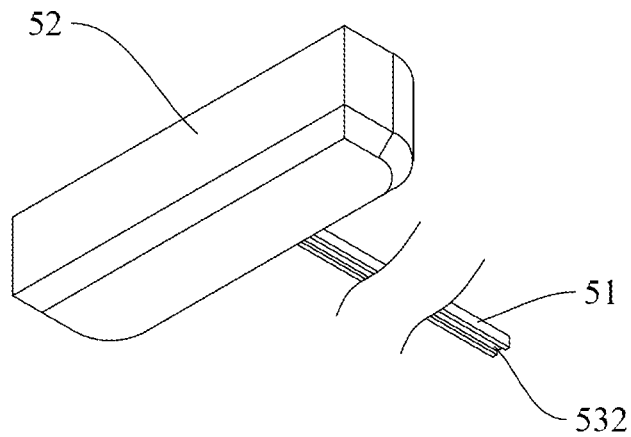

Please refer to FIG. 10 for perspective views of the tamper 500 according to embodiment 8 of the present invention.

The tamper 500 is configured to match the supporting member of the present invention and includes a slender shaft 51 and a grip portion 52 connected to the slender shaft 51. The tamper 500 serves to restore a fractured bone and press down a supporting member that has just been implanted.

As shown in the enlarged views of FIG. 10(a) and FIG. 10(b), the tamper 500 further includes a coupling and positioning structure 53 so as not to be shifted in position during operation. In this embodiment, the coupling and positioning structure 53 includes a fifth connecting portion 531 and a sixth connecting portion 532. The fifth connecting portion 531 is located at an upper side of the slender shaft 51 and/or the grip portion 52 and corresponds in shape to the second connecting portion of the supporting member of the present invention, and the sixth connecting portion 532 is located at a lower side of the slender shaft 51 and/or the grip portion 52 and corresponds in shape to the first connecting portion of the supporting member. As the third connecting portion and the fourth connecting portion of the insertion tool of the invention also correspond in shape to the second connecting portion and the first connecting portion of the supporting member of the invention respectively, the fifth connecting portion 531 of the tamper 500 can connect with the fourth connecting portion of the insertion tool of the invention in a sliding manner, and the sixth connecting portion 532 of the tamper 500 can connect with the third connecting portion of the insertion tool in a sliding manner. In one preferred embodiment, the connecting portions of the tamper of the invention have the same structures as the connecting portions of the supporting member of the invention (e.g., the upper connecting portion being a dovetail block, and the lower connecting portion being a dovetail groove) in order for the tamper to connect with the insertion tool.

The structure of the slender shaft 51 is preferably similar to but flatter than that of the supporting member of the present invention, and the dimensions of the slender shaft 51 may vary to meet practical needs. In fact, a plurality of tampers 500 whose slender shafts 51 vary in size may be used sequentially, in an ascending order of the shaft sizes, to either gradually push upward the top side of a collapsed fractured vertebra in order to restore the height of the vertebra, or press down a supporting member that has just been implanted so as to make room for the next supporting member to be implanted.

Please refer to FIG. 11 to FIG. 14 for schematic drawings showing how an implantation system 600 of the present invention is operated to implant a plurality of supporting members of the invention into a vertebra V or between two connected vertebrae V.

Figure 11:
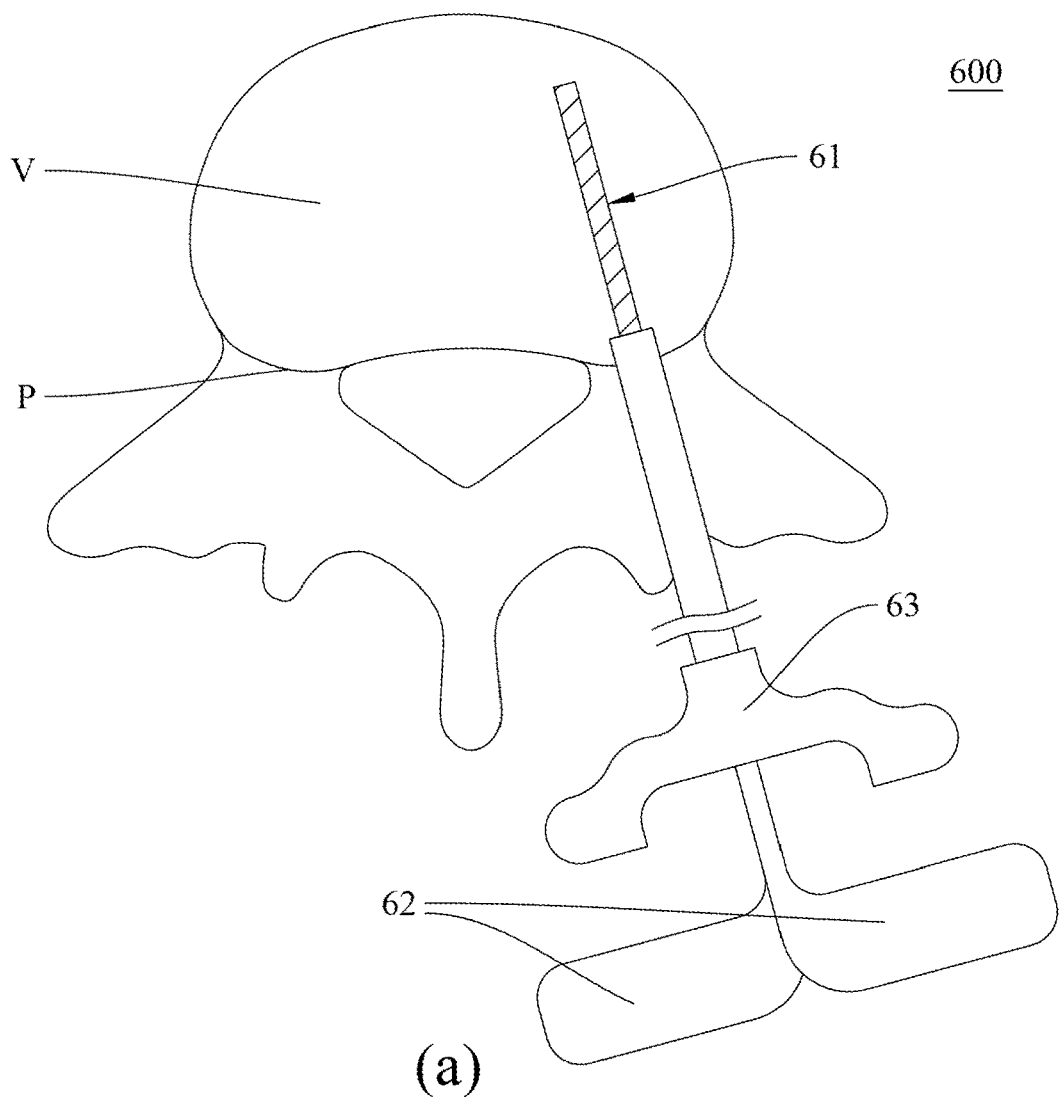
FIG. 11 shows schematic views of an implantation system according to a preferred embodiment of the present invention applied to a vertebra in (a) an axial view and (b) a left side view.
Figure 11:
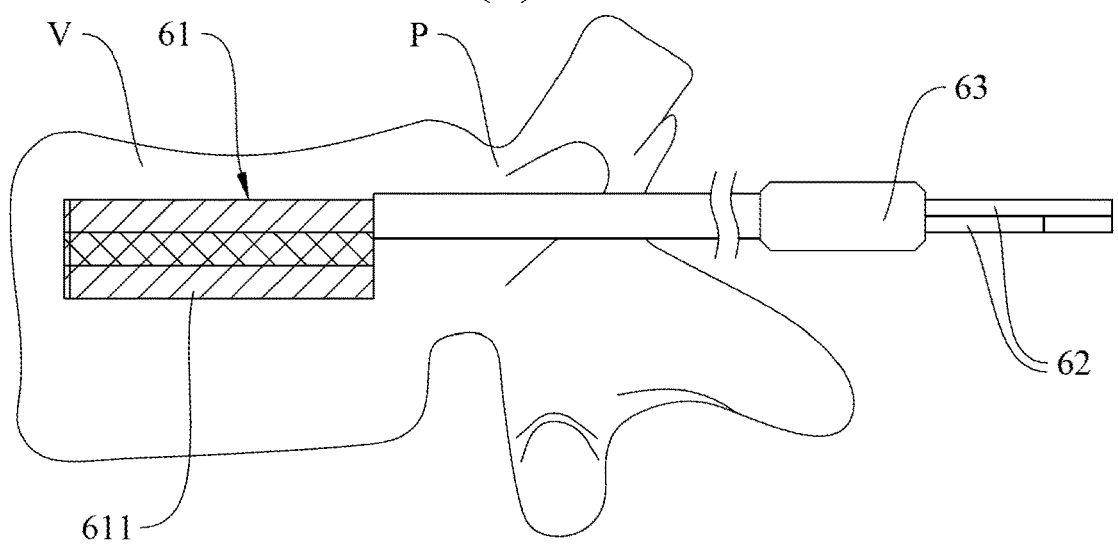

As shown in FIG. 11, the operation of implanting a plurality of supporting members of the present invention into a vertebra V begins by drilling a hole into the collapsed fractured vertebra V through one of its pedicles P and enlarging the hole using a series of introducers whose sizes are gradually increased. Once the hole is large enough, the working cannula 63 is placed into the hole, and the reamer is inserted through the working cannula 63 to remove the bone debris. Then, the tamper is used to restore the collapsed fractured vertebra V, and a supporting member 611 is subsequently introduced into the vertebra V (or between two connected vertebrae V if that is the case) by an insertion tool 62. After that, the tamper is used again to restore the collapsed fractured vertebra V and press down the supporting member 611, and another insertion tool 62 is used to introduce the next supporting member into the vertebra V (or between the two connected vertebrae V), connect this supporting member to the previous supporting member 611 in a sliding manner, and fasten the two supporting members together vertically.

Figure 12:
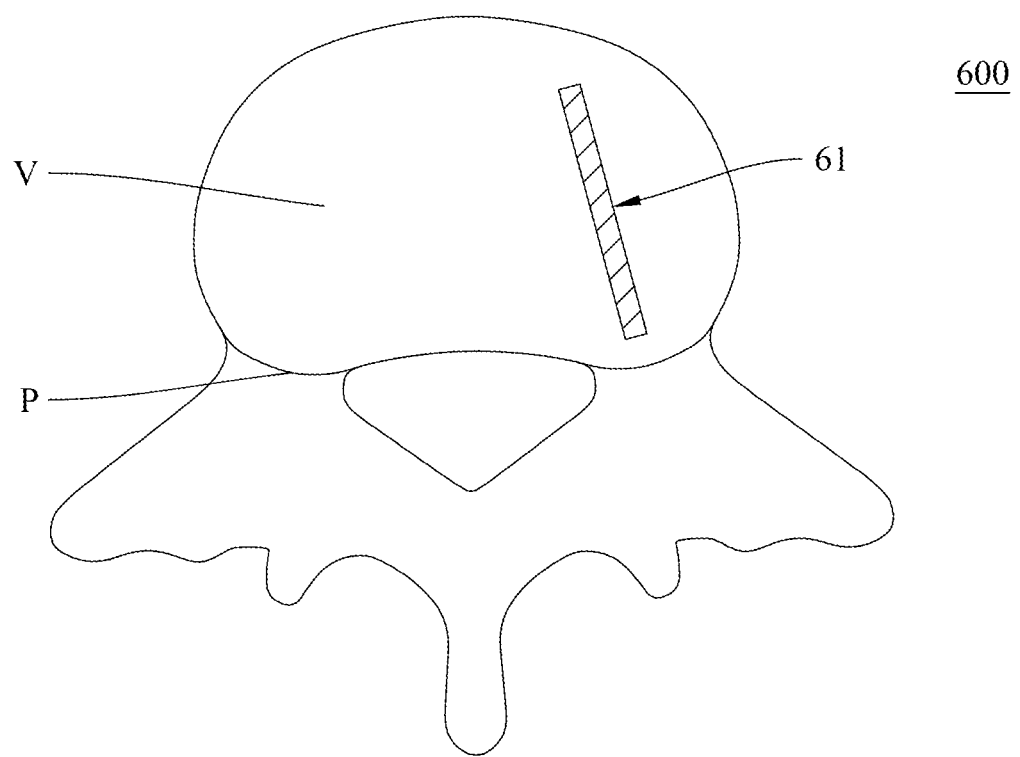
FIG. 12 shows (a) an axial view and (b) a left side view of a supporting member assembly according to a preferred embodiment of the present invention applied to a vertebra.
Figure 12:
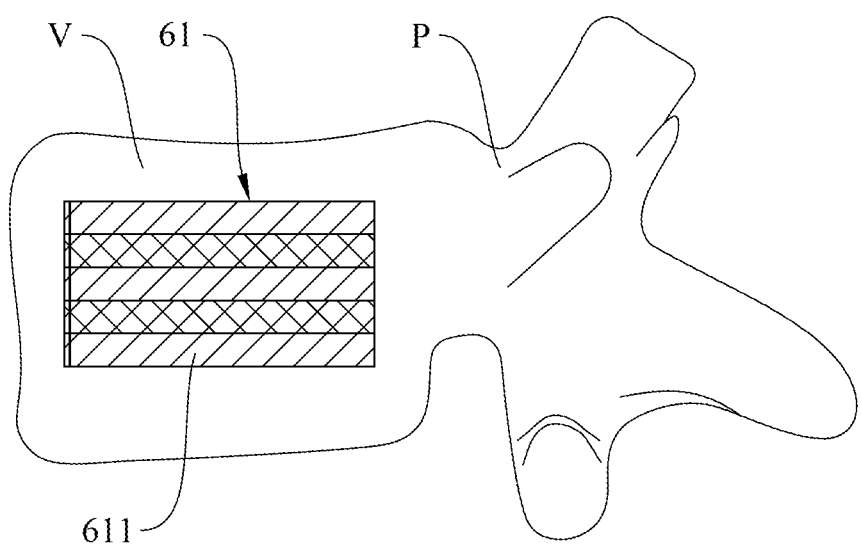
Figure 13:
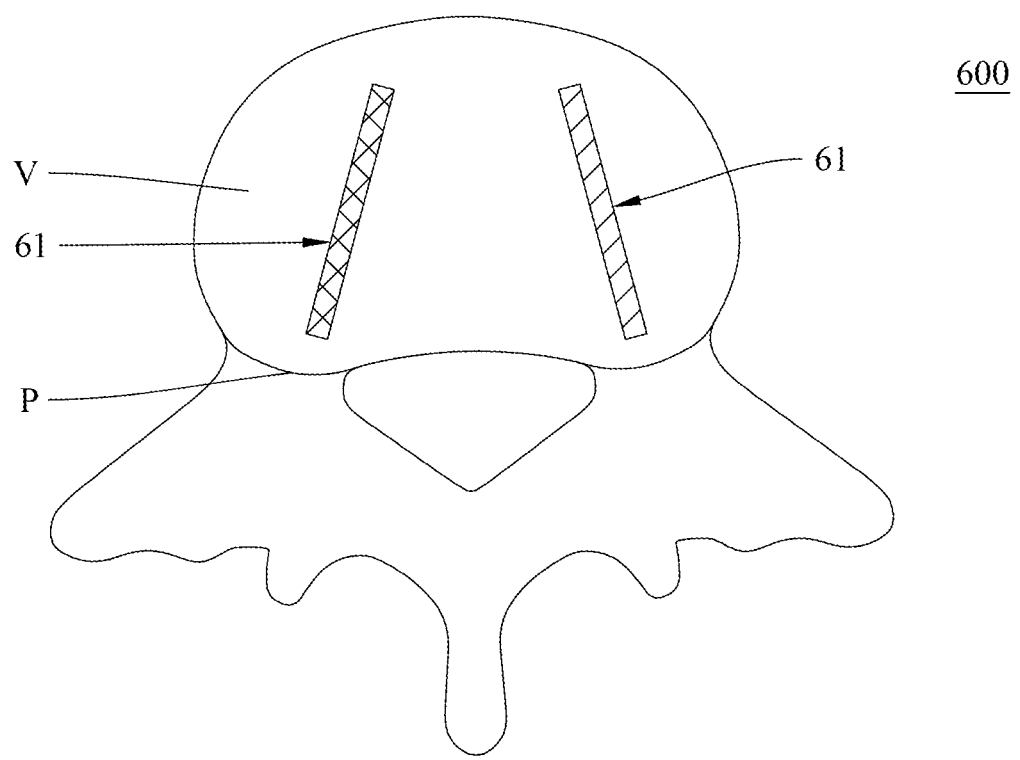
FIG. 13 shows (a) an axial view and (b) a left side view of a supporting member assembly according to a preferred embodiment of the present invention applied to a vertebra.
Figure 13:
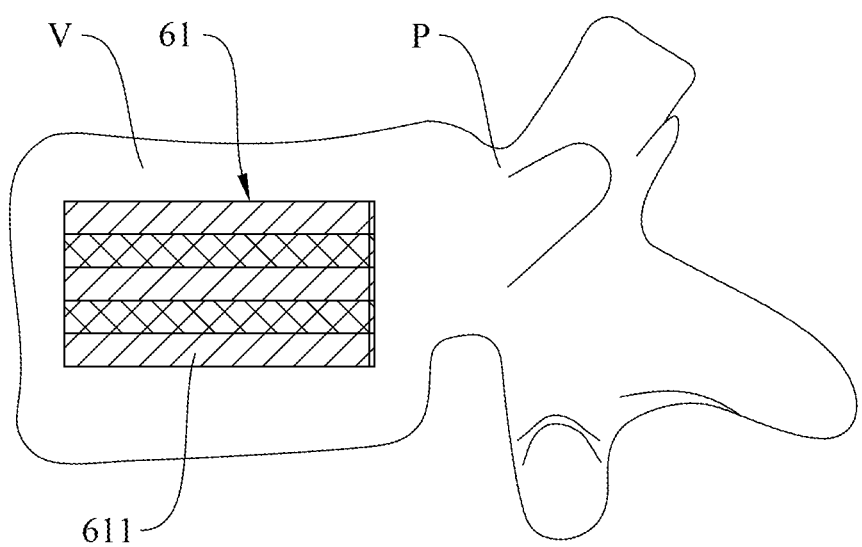
Figure 14:
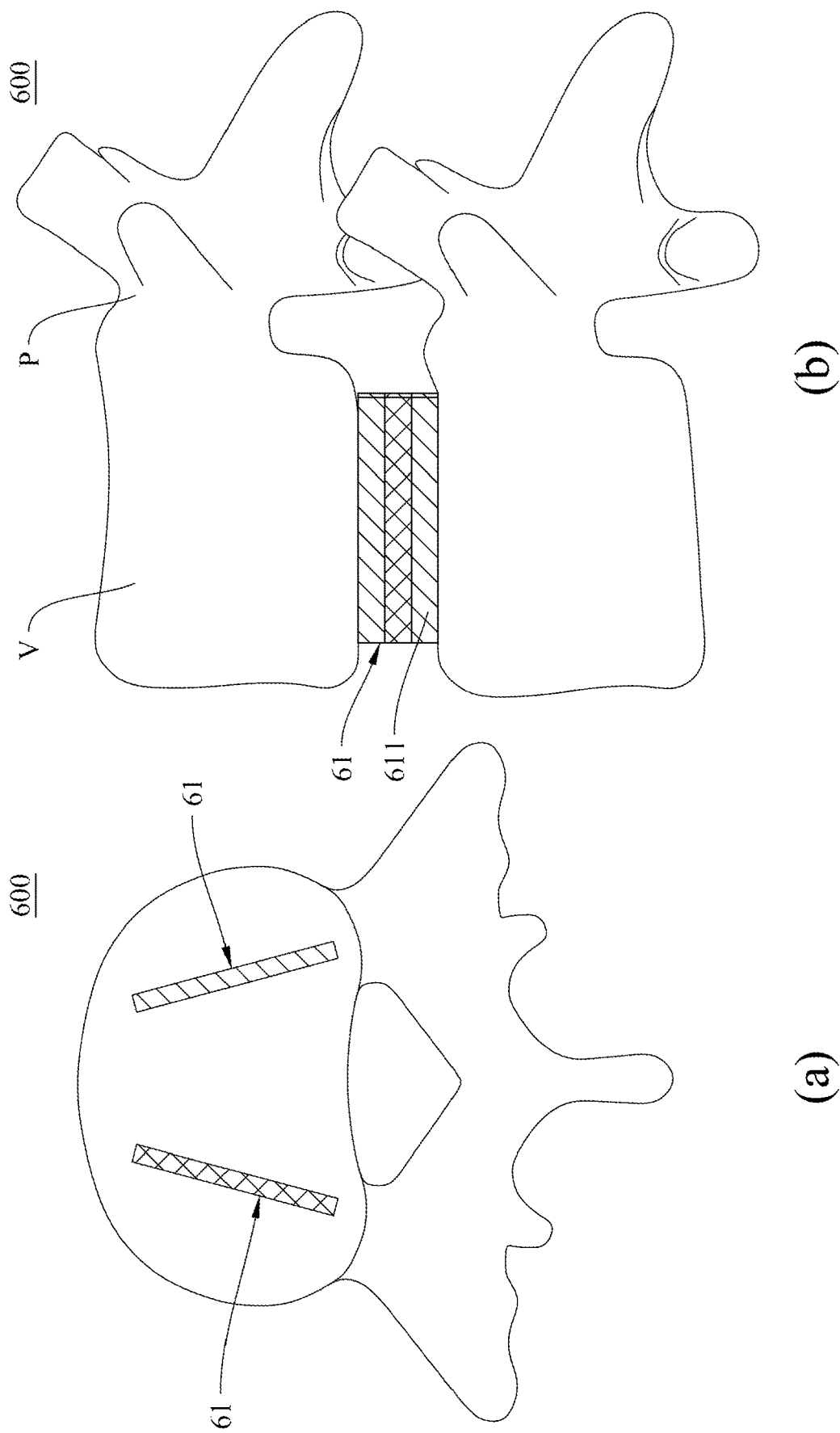
FIG. 14 shows (a) an axial view and (b) a left side view of a supporting member assembly according to a preferred embodiment of the present invention applied between connected vertebrae.

The present invention allows the supporting member 611 to be implanted into a subject's bone or between two connected bones, followed sequentially by more supporting members, which are connected to the supporting member 611 and to one another right in the bone or between the connected bones to form a supporting member assembly 61 (see FIG. 12). Depending on the extent of bone fracture and the supporting strength needed, two supporting member assemblies 61 may be implanted in a bilateral manner (see FIG. 13 and FIG. 14) to overcome such drawbacks of the conventional one-size implants as potential injury to the surrounding nerves and inadequate support.

In summary of the above, the present invention provides a supporting member that is configured as a micro-unit and whose small size allows not only implantation into a bone or between two connected bones, but also connection with other such members in the bone or between the connected bones so as to form a supporting member assembly, making possible a minimally invasive, small-incision surgical operation. In addition, the invention provides an introducer that can make and gradually enlarge a hole into a bone to enable the placement of a working cannula into the hole; a reamer for moving or pulling out bone debris; a tamper for restoring a fractured bone and pushing a previously implanted supporting member; and an insertion tool that can be used to introduce a supporting member into a bone or between two connected bones, connect this supporting member to its immediate predecessor in a sliding manner, and fasten the two supporting members together vertically, before the insertion tool is removed from the supporting members. The invention further provides a supporting member assembly that is formed by sequentially implanting and connecting a plurality of supporting members into a bone or between two connected bones so as to push outward the end plate(s) to be treated and thereby expand the fractured collapsed bone(s). This supporting member assembly is an improvement over the one-size implants used in the conventional implantation techniques on the grounds that an existing one-size implant cannot "be a single micro-unit before implantation into or between a subject's bones and connect with other similar micro-units sequentially implanted into or between the bones to form a larger yet complete block". Furthermore, unlike the traditional one-size implants, the supporting member assembly of the invention will not rupture the affected bone structure (e.g., a pedicle) or injure the surrounding nerves (e.g., the spinal cord or spinal nerves), blood vessels (e.g., the abdominal aorta or the vertebral arteries), or other important tissues (e.g., the ureters) during implantation, or provide inadequate support due to an expediently smaller-than-required size.

The above is the detailed description of the present invention. However, the above is merely the preferred embodiment of the present invention and cannot be the limitation to the implement scope of the present invention, which means the variation and modification according to the present invention may still fall into the scope of the invention.

What is claimed is:

1. An assembly, comprising:
   at least one supporting member for implantation into or between a subject's bones; and
   an insertion tool configured to guide the at least one supporting member into or between the subject's bones;
   wherein each at least one supporting member comprises a main body having two opposite sides defined respectively as an upper side and a lower side;
   a first connecting portion formed at the upper side of the main body and shaped as a male or female part of a dovetail joint;
   a second connecting portion formed at the lower side of the main body, shaped as the other of the male or female part of the dovetail joint and corresponding in shape to the first connecting portion; and
   a guiding structure formed at a side of the main body and configured to mate with the insertion tool;
   wherein a first supporting member of the at least one supporting member is vertically connectable with a second supporting member of the at least one supporting member such that the first connecting portion of the first supporting member is connectable with a second connecting portion of said second supporting member to form said dovetail joint;
   wherein a front side of the first connecting portion further includes a first positioning portion and a front side of the second connecting portion further includes a second positioning portion corresponding in shape and position to the first positioning portion;
   wherein the first positioning portion is a positioning block and the second positioning portion is a positioning hole;
   wherein the insertion tool comprises a plurality of connecting pins, an extension portion, and a grip portion, wherein the extension portion has one end connected to the plurality of connecting pins and an opposite end connected to the grip portion, wherein the extension portion and/or the grip portion comprises a third connecting portion, which is formed on an upper side of the extension portion and/or the grip portion, and is a dovetail projection, and a fourth connecting portion, which is formed on a lower side of the other of the extension portion and/or the grip portion, and is complementary in shape to the third connecting portion dovetail projection; and
   wherein the plurality of connecting pins can be correspondingly engaged with the guiding structure of each supporting member.

2. The assembly of claim 1, wherein the first connecting portion is a dovetail block and the second connecting portion is a dovetail groove configured to prevent the two first and second vertically connected supporting members from separating from each other after connecting in a sliding manner.

3. The assembly of claim 1, wherein a front side of the main body has a U-shaped groove structure that can be compressed or deformed to facilitate fastening between the two first and second vertically connected supporting members and return to an original shape elastically to prevent the two first and second vertically connected supporting members from separating from each other.

4. The assembly of claim 1, wherein the guiding structure includes a plurality of guiding holes and/or buffer grooves.

5. The assembly of claim 4, wherein the plurality of guiding holes and/or buffer grooves have various designs with a difference in angle, position, size, or shape.

6. The assembly of claim 1, wherein the main body comprises at least one reticulated structure.

7. The assembly of claim 6, wherein the at least one reticulated structure can be filled with a bone-filling material or bone cement.

8. The assembly of claim 1, wherein the bones are vertebrae.

9. The assembly of claim 1, wherein a material of the at least one supporting member includes metal, plastic, or a mixture thereof.

10. The assembly of claim 1, wherein the insertion tool further comprises a buffer base.

11. The assembly of claim 1, wherein the plurality of connecting pins of the insertion tool comprises two connecting pins that correspond in design to but are different from the guiding structure of each supporting member in angle, position, shape, or size.

12. The assembly of claim 1, wherein the third connecting portion of the insertion tool can correspond to the second connecting portion of the at least one supporting member and the fourth connecting portion can correspond to the first connecting portion of the at least one supporting member so that the insertion tool can be pushed along and coupled with the each supporting member in a sliding manner.

13. The assembly of claim 1, wherein the at least one supporting member comprises a plurality of supporting members, including the first and second supporting members, sequentially connected, wherein the first connecting portion of the first supporting member is slidably connected with the second connecting portion of the second supporting member such that the dovetail joint is formed between said first and second supporting members in order to connect the plurality of supporting members sequentially.

14. A tamper, used in conjunction with the assembly of claim 1, comprising a slender shaft and a grip portion connected to the slender shaft; wherein, an upper side of the slender shaft and/or the grip portion further includes a fifth connecting portion corresponding to the second connecting portion of the at least one supporting member, and a lower side of the slender shaft and/or the grip portion further includes a sixth connecting portion corresponding to the first connecting portion of the at least one supporting member.

\* \* \* \* \*